United States Patent
Miyasaka et al.

(10) Patent No.: US 12,414,977 B2
(45) Date of Patent: Sep. 16, 2025

(54) METHOD OF ADMINISTERING SEABERRY AND SAW PALMETTO EXTRACTS TO INHIBIT 5α-REDUCTASE ACTIVITY

(71) Applicant: ORYZA OIL & FAT CHEMICAL CO., LTD., Aichi (JP)

(72) Inventors: Kenchi Miyasaka, Aichi (JP); Norihito Shimizu, Aichi (JP); Hiroshi Shimoda, Aichi (JP); Hiromichi Murai, Aichi (JP)

(73) Assignee: ORYZA OIL & FAT CHEMICAL CO., LTD., Aichi (JP)

( * ) Notice: Subject to any disclaimer, the term of this patent is extended or adjusted under 35 U.S.C. 154(b) by 491 days.

(21) Appl. No.: 17/772,232

(22) PCT Filed: May 1, 2020

(86) PCT No.: PCT/JP2020/018401
§ 371 (c)(1),
(2) Date: Apr. 27, 2022

(87) PCT Pub. No.: WO2021/145004
PCT Pub. Date: Jul. 22, 2021

(65) Prior Publication Data
US 2022/0370539 A1    Nov. 24, 2022

(30) Foreign Application Priority Data
Jan. 16, 2020 (JP) .................................. 2020-005114

(51) Int. Cl.
| | | |
|---|---|---|
| *A61K 36/889* | (2006.01) | |
| *A23L 33/105* | (2016.01) | |
| *A61K 8/9789* | (2017.01) | |
| *A61K 8/9794* | (2017.01) | |
| *A61K 36/185* | (2006.01) | |
| *A61P 13/08* | (2006.01) | |
| *A61P 17/10* | (2006.01) | |
| *A61P 17/14* | (2006.01) | |
| *A61Q 7/00* | (2006.01) | |
| *A61Q 19/00* | (2006.01) | |

(52) U.S. Cl.
CPC .......... *A61K 36/889* (2013.01); *A23L 33/105* (2016.08); *A61K 8/9789* (2017.08); *A61K 8/9794* (2017.08); *A61K 36/185* (2013.01); *A61P 13/08* (2018.01); *A61P 17/10* (2018.01); *A61P 17/14* (2018.01); *A61Q 7/00* (2013.01); *A61Q 19/00* (2013.01)

(58) Field of Classification Search
CPC .. A61K 36/889; A61K 8/9794; A61K 8/9789; A61K 36/185; A23L 33/105; A61P 1/10; A61P 13/08; A61P 17/14; A61Q 7/00; A61Q 19/00
See application file for complete search history.

(56) References Cited

FOREIGN PATENT DOCUMENTS

| | | | | |
|---|---|---|---|---|
| CN | 108186511 A | * | 6/2018 | ............... A61K 8/42 |
| JP | 62-093215 | | 4/1987 | |
| JP | 63-93215 | | 4/1987 | |
| JP | 05-097684 | | 4/1993 | |
| JP | 2002-525080 | | 8/2002 | |
| JP | 2007-099751 | | 4/2007 | |
| JP | 2007-161645 | | 6/2007 | |
| JP | 2007-514789 | | 6/2007 | |
| JP | 2010-511066 | | 4/2010 | |
| JP | 2015-028044 | | 2/2015 | |
| JP | 2016-216369 | | 12/2016 | |
| KR | 10-2018-0105290 | | 9/2018 | |
| WO | WO-2015061860 A1 | * | 5/2015 | ........... A61K 31/198 |

OTHER PUBLICATIONS

Machine translation of JP-2007161645-A from PE2E via FIT, 2007 (Year: 2007).*
Machine translation of CN 108186511 A provided from PE2E via FIT (Year: 2018).*
M. Suzuki et al., "Clinical Evaluation of Hair Regrowth Tonics Containing Oleanolic Acid", vol. 31, No. 4, 1989.
M. Shimizu et al., "Development of Seaberry Extract, and Its Functions", vol. 51, No. 9, 2016.
Supervised by Momokazu GOTO, Benign Prostatic Hyperplasia Drug, Health Care Science Institute, 2014.
J. Liu et al., "5a-Reductase Inhibitory . . . from Ganoderma Lucidum", Pharmaceutical Society of Japan, 22006.

* cited by examiner

*Primary Examiner* — Bethany P Barham
*Assistant Examiner* — Ayaan A Alam
(74) *Attorney, Agent, or Firm* — Millen, White, Zelano & Branigan, P.C.; Christopher W. Brody

(57) ABSTRACT

A 5α-reductase inhibitor contains saw palmetto extract and seaberry extract as an active ingredient in a synergistic compounding ratio, wherein the compounding ratio by weight of the saw palmetto extract and the seaberry extract is 3:1~2. The 5α-reductase inhibitor containing the saw palmetto extract and seaberry extract or just the seaberry extract as a 5α-reductase inhibitor can be administered to the human body in order to inhibit 5α-reductase. The 5α-reductase inhibitor is useful as a prostate enlargement inhibitor, an androgenic alopecia inhibitor, and an acne prevention and amelioration agent. The 5α-reductase inhibitor can be part of a food or drink composition or a cosmetic composition.

3 Claims, No Drawings

METHOD OF ADMINISTERING SEABERRY AND SAW PALMETTO EXTRACTS TO INHIBIT 5α-REDUCTASE ACTIVITY

TECHNICAL FIELD

The present invention relates to a novel combination of 5α-reductase inhibitors. The present invention is widely used in foods, pharmaceuticals, cosmetics, and the like.

BACKGROUND ART

The prostate gland is located just below the bladder in men and is the organ that surrounds the posterior urethra. Prostate enlargement is caused by a decrease in male hormones with age. Prostate hypertrophy is thought to be caused by the accumulation of dihydrotestosterone (DHT). DHT is produced by the conversion of testosterone by 5α-reductase. When testosterone is taken up into prostate cells, it is converted to DHT by 5α-reductase present in the prostate cells, and DHT promotes cell proliferation. As a result, the prostate enlarges (benign prostatic hyperplasia) and causes dysuria (Patent Document 2). Therefore, inhibition of 5α-reductase, which is a DHT (active) synthase in cell proliferation, is significant in suppressing dysuria associated with benign prostatic hyperplasia (Non-Patent Documents 1 to 3).

In addition, testosterone biosynthesized in the testicles, or the like is converted to dihydrotestosterone in the head by 5α-reductase present in hair follicles, sebaceous glands, or the like. The dihydrotestosterone significantly reduces the activity of adenylcyclase, resulting in a decrease in intracellular cyclic AMP levels, thus resulting in a decrease in energy production and suppression of protein synthesis in and around the hair. It is believed that this process promotes androgenetic alopecia (Patent Document 2).

Therefore, recently, there is a tendency to pay attention to the characteristics of a substance, for example, the 5α-reductase inhibitory effect, hair matrix cell-activating effect, and blood circulation promoting effect, and to use the substance as a hair growing and nourishing agent.

Further, in recent years, the desire of people to be beautiful, healthy, and youthful, regardless of age or gender, has become stronger. Then, in the age group of 11 to 25 years old, acne is a crucial matter that should not be excluded from the viewpoint of beautiful skin. Acne is formally called acne vulgaris. 70 to 80% of patients are concentrated in the age group of 11-25 years, and it can also be said that mild acne is one of the characteristics of adolescent skin rather than skin disease. However, severe acne is unsightly and often leaves acne scars even after having healed, and for some people, acne alone often makes them psychologically depressed, and it often affects even their daily life and social activities. Therefore, from a cosmetic point of view, it is necessary to take appropriate measures as soon as possible to restore normal and clean skin.

It is also considered that dihydrotestosterone produced by 5α-reductase from testosterone is involved in the development and exacerbation of acne, and if a drug having a 5α-reductase inhibitory action can suppress or inhibit the production of dihydrotestosterone, occurrence or exacerbation of acne can be suppressed (Patent Document 3).

PRIOR ART

Patent Documents

Non-Patent Document 1: Supervised by Momokazu GOTO, Edited by The Health Care Science Institute, Kusuri ga mieru, 1, Published by Medic Media Co., Ltd., P436-438 (2014).

Non-Patent Document 2: Jie L., et. Al., Biol. Pharm. Bull., 29 (2), P392-395 (2006).
Non-Patent Document 3: Koseki J., et. Al., Hindawi Publishing Corporation, 2015, ID 853846 (2015).
Patent Document 1: Japanese Published Unexamined Patent Application No. 2015-028044
Patent Document 2: Japanese Published Unexamined Patent Application No. 5-0976484
Patent Document 3: Japanese Published Unexamined Patent Application No. 2007-099751

SUMMARY OF THE INVENTION

Problems to be Solved by the Invention

The present invention is to solve the above-described problems and to provide a new 5α-reductase inhibitor.

Means to Resolve the Problems

The features of the present invention for solving the above problems are as follows.
1. A 5α-reductase inhibitor containing seaberry (*Hippophae Rhamnoides Rhamnoides*) extract as an active ingredient.
2. A 5α-reductase inhibitor containing seaberry extract and saw palmetto (Serenoa Repens) extract as an active ingredient in a synergistic compounding ratio.
3. A 5α-reductase inhibitor according to the above item 2, wherein the compounding ratio by weight of the saw palmetto extract and the seaberry extract (saw palmetto extract: seaberry extract) is 3~1:1~2.
4. A prostate enlargement inhibitor containing the 5α-reductase inhibitor as an active ingredient, according to any one of the above-mentioned items 1 to 3.
5. An androgenic alopecia inhibitor containing the 5α-reductase inhibitor as an active ingredient, according to any one of the above-mentioned items 1 to 3.
6. An acne prevention and amelioration agent containing the 5α-reductase inhibitor as an active ingredient, according to any one of the above-mentioned items 1 to 3.
7. A food or drink composition for inhibiting 5α-reductase containing the 5α-reductase inhibitor as an active ingredient, according to any one of the above-mentioned items 1 to 3.
8. A cosmetic composition for inhibiting 5α-reductase containing the 5α-reductase inhibitor as an active ingredient, according to any one of the above-mentioned items 1 to 3.
9. A method for inhibiting 5α-reductase activity in a human body, wherein an effective amount of seaberry extract is administered to the human body.
10. A method for inhibiting 5α-reductase activity in a human body, wherein an effective amount of seaberry extract and saw palm extract, in a compounding ratio that exhibits a synergistic effect, is administered to the human body.
11. A method for inhibiting 5α-reductase activity according to the above-mentioned item 10, wherein the compounding ratio by weight of the saw palmetto extract and the seaberry extract (saw palmetto extract: seaberry extract) is 3~1:1~2.
12. A method for inhibiting 5α-reductase activity according to any one of the above-mentioned items 9 to 11, which is used for the human body to suppress benign prostatic hyperplasia, androgenetic alopecia, and to prevent and ameliorate acne.

Effects of the Invention

According to the present invention, containing the seaberry extract as an active ingredient makes it possible to have a 5α-reductase inhibitory effect.

Also, according to the present invention, containing the seaberry extract and the saw palmetto extract in a compounding ratio exhibiting a synergistic action makes it possible to efficiently have a 5α-reductase inhibitory effect, thus making it possible to provide a 5α-reductase inhibitor having an even better effect. Further, according to the present invention, setting the compounding ratio by weight of the saw palmetto extract and the seaberry extract (saw palmetto extract: seaberry extract) to 3~1:~2 makes it possible to provide a 5α-reductase inhibitor having further excellent synergism. Further, the present invention allows for having an excellent 5α-reductase inhibitory action, so that the conversion of testosterone to DHT by 5α-reductase is inhibited, and then the proliferation of prostate cells caused by DHT is suppressed, thus making it possible to have an excellent effect of suppressing benign prostatic hyperplasia. Furthermore, the present invention allows for having an excellent 5α-reductase inhibitory action, so that testosterone suppresses the production of dihydrotestosterone by 5α-reductase present in hair follicles, sebaceous glands, etc. in the head. This reduces the activity of adenylcyclase and suppresses the decrease in intracellular cyclic AMP level, and as a result, suppresses the decrease in energy production in and around the hair and induces protein synthesis, thus suppressing the progression of androgenetic hair loss. Therefore, it is possible to provide an excellent androgenetic alopecia inhibitor. In addition, such a 5α-reductase inhibitory action makes it possible to suppress the production of dihydrotestosterone, thereby suppressing the development and exacerbation of acne.

MODES FOR CARRYING OUT THE INVENTION

Hereinafter, the present invention will be described in detail. The present invention is characterized in that seaberry extract is used as an active ingredient. The seaberry (*Hippophae rhamnoides L.*) is the plant of the genus *Hippophae* of the family Elaeagnaceae.

When preparing a seaberry extract, the target part of the plant to be extracted is not particularly limited, and appropriate parts such as seeds, fruits, leaves, bark, stems, roots, and above-ground parts can be used, but especially among them, fruits are the most preferable. As an extraction method, if necessary, the target part to be extracted can be washed in advance with water, then dried, chopped, or crushed, and then brought into contact with an extraction solvent according to a conventional method such as a dipping method or a counter-current extraction method.

Examples of the extraction solvent for the extract include alcohols such as methanol, ethanol, propanol, butanol, or the like; glycols such as 1,3-butylene glycol, glycerin, propylene glycol, or the like; esters such as ethyl acetate, butyl acetate or the like; esters such as ethyl ether, propyl ether, isopropyl ether, tetrahydrofuran, dioxane or the like; halogenated hydrocarbons such as dichloromethane, chloroform or the like; ketones such as acetone, methyl ethyl ketone, diethyl ketone, cyclohexanone or the like; hexane, cyclohexane, petroleum ether, water or the like. Among these, ethanol, 1,3-butylene glycol, water, acetone, dichloromethane, or the like is preferably used. These solvents can be used alone or in an admixture of two or more. When the solvents are mixed and used, the mixing ratio of each solvent may be appropriately adjusted according to the type of the solvent.

The extraction method is not particularly limited, and a heating extraction method in which a solvent (for example, ethanol) is added to the fruit of seaberry and then heated to the extent that the activity of the active ingredient contained in the extract is not inactivated, or supercritical extraction method or the like can be appropriately applied. Further, various known extraction methods, such as a dipping extraction method in which fruits of the genus *Hippophae* of the family Elaeagnaceae are immersed in a fixed amount of solvent for batch treatment, a continuous extraction method in which the solvent is continuously sent, or the like can be applied.

To give an example of a specific extraction method, for example, an extraction solvent of about 5 to 50 times by weight, preferably about 10 to 40 times by weight of the dry weight of seaberries is added and immersed in the seaberries to heat them at 25 to 100 degrees Celsius and to stir the solvent for about one to six hours until the active ingredient can be extracted. Of course, the type of solvent, the amount of solvent, the heating temperature, the heating time, and the like may be appropriately adjusted so that the active ingredient can be efficiently extracted. In addition, the seaberry extract preferably contains at least one of oleanolaldehyde, oleanolic acid, ursolic acid, pomolic acid, uvaol, isorhamnetin, and 7-O-ramnoside.

Also, the present invention is characterized by combining a seaberry extract and a saw palmetto extract. In this case, the same seaberry extract as described above can be used. Saw palmetto is a plant belonging to Trachycarpus of Arecaceae, and its scientific name is Serenoa repens, and it is also called Sabal serrulata. It is more preferable to use ripe fruits as the raw material for the saw palmetto extract.

Saw palmetto extract can be obtained by an extraction method commonly used for plant extraction. To obtain the saw palmetto extract, for example, raw or dried saw palmetto fruit is immersed in the extraction solvent, or the raw or dried saw palmetto fruit is crushed by a coarse crusher, then immersed in the extraction solvent. As the solvent used for extraction, it is preferable to use any one of water, a hydrophilic organic solvent, and a mixed solvent thereof at room temperature or at a temperature of about the boiling point of the solvent. Examples of the hydrophilic organic solvent include lower alcohols having 1 to 5 carbon atoms such as methanol, ethanol, propyl alcohol, isopropyl alcohol or the like; lower aliphatic ketones such as acetone, methyl ethyl ketone or the like; polyhydric alcohols having 2 to 5 carbon atoms such as 1,3-butylene glycol, propylene glycol, glycerin or the like. A mixed solvent of these hydrophilic organic solvents and water can be used. Extraction can be performed under reflux heating using any device according to the type of solvent and the extraction scale. A commercially available product, e.g., a purified saw palmetto extract manufactured by Indena S.p.A. can also be used as the saw palmetto extract.

It is desirable that the saw palmetto extract and the seaberry extract are both combined in a compounding ratio that exhibits a synergistic effect. The compounding ratio by weight of the saw palmetto extract and the seaberry extract is not particularly limited, but for example, the ratio can be like saw palmetto extract:seaberry extract=3~1:1~2, preferably 3:1~2, most preferably 3:2, thus making it possible to maximize the synergistic effect of 5α-reductase inhibition.

The 5α-reductase inhibitor of the present invention can be used as a material for various foods and drinks (i.e., food and drink compositions for inhibiting 5α-reductase).

For example, such foods and drinks include general foods such as edible oils (salad oil); confectionery (gums, candies, caramels, chocolates, cookies, snacks, jellies, gummies, tablet confectionery, or the like); noodles (soba noodles, udon noodles, ramen noodles or the like); dairy products (milk, ice cream, yogurt or the like); seasonings (miso, soy sauce or the like); soups; beverages (juice, coffee, black tea, tea, carbonated beverages, sports beverages, or the like); health foods (e.g., tablets, capsules or the like); and nutritional supplements (nutrition drinks or the like). The 5α-reductase inhibitor of the present invention may be appropriately blended with the above-mentioned foods and drinks.

Various components can be blended into the above-mentioned foods and drinks according to their types. It is possible to use food materials, for example, glucose, fructose, sucrose, maltose, sorbitol, stevioside, corn syrup, lactose, citric acid, tartrate acid, apple acid, succinic acid, lactic acid, L-ascorbic acid, dl-α-tocopherol, sodium erythorbate, glycerin, propylene glycol, glycerin fatty acid ester, polyglyceryl fatty acid ester, sucrose fatty acid ester, sorbitan fatty acid ester, propylene glycol fatty acid ester, Arabic gum, carrageenan, casein, gelatin, pectin, agar-agar, vitamin Bs, nicotinic acid amides, calcium pantothenate, amino acids, calcium salts, pigments, fragrances, preservatives or the like.

Further, the 5α-reductase inhibitor having a health maintenance function can also be blended with other antioxidants, health food materials, or the like such as reduced ascorbic acid (vitamin C), vitamin E, reduced glutatin, tocotrienol, vitamin A derivative, lycopene, beta-cryptoxanthin, astaxanthin, zeaxanthin, fucoxanthin, uric acid, ubiquinone, Coenzyme Q10, folic acid, garlic extract, allicin, sesamin, lignans, catechin, isoflavone, chalcon, tannins, flavonoids, coumarin, isokmarins, blueberry extract, V. (vitamin) A, V.B1, V.B2, V.B6, V.B12, V.C, V.D, V.E, V.P, choline, niacin, pantothenic acid, calcium folic acid, EPA, oligosaccharides, dietary fiber, squalene, soybean lecithin, taurine, dunaliela, protein, octacosanol, DHA, egg yolk lecithin, linoleic acid, lactoferrin, magnesium, zinc, chromium, selenium, potassium, heme iron, oyster meat extract, chitosan, chitin oligosaccharide, collagen, chondroitin, turmeric, elastin, sweetroot, Lycium chinese fruit, cinnamon cassia, Crataegus oxyacantha, ginger, bracket fungus, corbicula extract, chinese soft-shell turtle, plantain, chamomile, dandelion, hibiscus, honey, Boren, royal jelly, lime, lavender, rosehip, rosemary, sage, bifidobacteria, facaris, Bacillus coagulans SANK 70258, wheat germ oil, sesame oil, perilla oil, soybean oil, medium chain fatty acids, agaricus, ginkgo leaf extract, chondroitin, brown rice germ extract, lychee, onion, DHA, EPA, DPA, Tencha tea, Ophiocordyceps sinensis, garlic, wasp larva, papaya, puerh tea, propolis, Acer maximowiczianum, Hericium erinaceum, Royal jelly, saw palmetto, hyaluronic acid, collagen, gaba, harp seal oil, shark cartilage, glucosamine, lecithin, phosphatidylserine, Panax notoginseng, mulberry leaves, soybean extract, echinacea, Acanthopanax senticosus Harms, barley extract, olive leaf, olive fruit, gymnema, Lagerstroemia speciosa, salacia, garcinia, chitosan, St. John's wort, Chinese date, carrot, passion flower, broccoli, placenta, adlay, grape seed, peanut testa, bilberry, black cohosh, milk thistle (Silybum marianum), laurel, sage, rosemary, Apocynum venetum, black vinegar, bitter gourd, maca, safflower, flax, oolong tea, flower thorn, caffeine, capsaicin, xylooligosaccharide, glucosamine, buckwheat, citrus, dietary fiber, protein, prune, spirulina, barley young leaf, nucleic acid, yeast, shiitake mushroom, plum meat, amino acid, deep-sea shark extract, noni, oyster meat, Chinese softshell turtle (terrapin), champignon, plantain, acerola, pineapple, banana, peach, apricot, melon, strawberry, raspberry, orange, fucoidan, Fomes yucatensis, cranberry, chondroitin sulfate, zinc, iron, ceramide, silk peptides, glycine, niacin, chastetree, ceramide, L-cysteine, L-carnitine, red wine juice, millet, horsetail, biotin, centela asiatica, Lonicera caerulea L. pycnogenol, Japanese butterbur, rhubarb, clove, rosemary, catechin, puerh tea, citric acid, beer yeast, melilot, black ginger, ginger, zedoaria, nattokinase, monascuc, tocotrienol, lactoferrin, tartary buckwheat, cocoa, Houttuynia, kiwi fruit, long pepper, lotus leaf, Pfaffia, star fruit or the like.

As a specific manufacturing method, the above-mentioned extracts (seaberry extract, saw palmetto extract) are spray-dried or freeze-dried together with powdered cellulose to make them into powder, granules, tablets, or solution, thus making it possible to easily blend them with foods and drinks (instant foods or the like).

Since the major purpose of the present invention is to prevent diseases and maintain health, when applying the 5α-reductase inhibitor to the foods and drinks, the content of the active ingredient should preferably be 1 to 20 wt % or less in total.

The 5α-reductase inhibitor of the present invention may be used as a material for drugs (including pharmaceuticals and quasi-drugs), which can be produced by appropriately blending the 5α-reductase inhibitor of the present invention with raw material for a pharmaceutical preparation.

Examples of the pharmaceutical raw material that can be blended with the 5α-reductase inhibitor of the present invention include e.g. vehicles (glucose, lactose, sucrose, sodium chloride, starch, calcium carbonate, kaolin, crystalline cellulose, cacao oil, hydrogenated vegetable oil, talc or the like), binders (distilled water, normal saline solution, ethanolic solution, simple syrup, glucose solution, starch solution, gelatin solution, carboxymethyl cellulose, potassium phosphate, polyvinyl pyrrolidone, or the like), disintegrating agent (sodium alginate, agar-agar, sodium-hydrogen carbonate, calcium carbonate, sodium-lauryl sulphate, monoglyceride stearate, starch, lactose, gum arabic powder, gelatin, ethanol, or the like), disintegration-suppressive agent (sucrose, stearin, cacao oil, hydrogenated oil, or the like), absorption promoters (quaternary-ammonium base, sodium lauryl sulphate, or the like), adsorbents (glycerin, starch, lactose, kaolin, bentonite, silica acid, or the like), lubricant agents (purified talc, stearate, polyethylene glycol, or the like) or the like.

The method for administering the 5α-reductase inhibitor according to the present invention may generally be an oral administration in the form of tablets, pills, soft/hard capsules, fine granules, powders, granules, liquids, and the like. However, the method may also be done by a parenteral administration, which is applied in the form of a solution, or with the addition of dispersants, suspensions, stabilizers, or the like, thus making them into the form of haptics, lotions, ointments, tinctures, creams, or the like.

The dose may vary depending on the administration method, medical condition, age of the patient, or the like. Adults can usually take approximately 1.0 to 1,000 mg of the active ingredient per day and children usually can take approximately 0.5 to 500 mg per day. The compounding ratio of the 5α-reductase inhibitor can be appropriately changed depending on the dosage form. Normally, it is preferably about 0.3 to 15.0 wt % when administered orally or by mucosal absorption, and also preferably 0.01 to 10 wt % when administered parenterally. The dose varies depending on various conditions. A dose smaller than the above dose may be sufficient, but it may also be necessary to administer beyond the range described above.

Examples of the form of the external skin preparation (cosmetic composition for inhibiting 5α-reductase) containing the 5α-reductase inhibitor of the present invention include milky lotions, soaps, face washes, bathing agents, creams, milky lotions, lotions, eau de Colognes, shaving creams, shaving lotions, cosmetic oils, suntan/sunscreen lotions, whitening powders, foundations, perfumes, packs, nail creams, enamels, enamel removers, eyebrow pencils, blushes, eye creams, eye shadows, mascaras, eyeliners, lip balms (lip creams), shampoos, hair conditioners, hair treatment agents, hair-dyeing agents, dispersions, cleaning agents or the like. In addition, examples of the pharmaceutical products or quasi-drugs to which the 5α-reductase inhibitor of the present invention can be blended include ointments, creams, external liquids, or the like.

For the above-mentioned form of the external skin preparation, in addition to the 5α-reductase inhibitor according to the present invention, it is also possible, as long as the 5α-reductase inhibitory effect is not impaired, to blend a component to be added to the external skin preparation such as cosmetics and quasi-drugs, oils, higher alcohols, fatty acids, UV absorbers, powders, pigments, surfactants, polyhydric alcohols/sugars, polymers, physiologically active ingredients, solvents, antioxidants, fragrances, preservatives, or the like. Examples will be listed below, but the invention is not limited to these examples.

(1) Specific Examples of Oil

Ester-type oil phase ingredient includes: glyceryl tri-2-ethylhexanoate, cetyl 2-ethylhexanoate, isopropyl myristate, butyl myristate, isopropyl palmitate, ethyl stearate, octyl palmitate, isocetyl isostearate, butyl stearate, butyl myristate, ethyl linoleate, isopropyl linoleate, ethyl oleate, isocetyl myristate, isostearyl myristate, isostearyl palmitate, octyl dodecyl myristate, isocetyl isostearate, diethyl sebacate, diisopropyl adipate, isoaralkyl neopentanoate, glyceryl tri (caprylate/caprate), trimethylolpropane tri-2-ethylhexanoate, trimethylolpropane triisostearate, pentaerythritol tetra-2-ethylhexanoate, cetyl caprylate, decyl laurate, hexyl laurate, decyl myristate, myristyl myristate, cetyl myristate, stearyl stearate, decyl oleate, cetyl ricinoleate, isostearyl laurate, isotridecyl myristate, isocetyl myristate, isostearyl myristate, isocetyl palmitate, isostearyl palmitate, octyl stearate, isocetyl stearate, isodecyl oleate, octyldodecyl oleate, octyldodecyl linoleate, isopropyl isostearate, cetostearyl 2-ethylhexanoate, stearyl 2-ethylhexanoate, hexyl isostearate, ethylene glycol dioctanoate, ethylene glycol dioleate, propylene glycol dicaprate, propylene glycol di caprylate/dicaprate), propylene glycol dicaprylate, neopentyl glycol dicaprate, neopentyl glycol dioctanoate, glyceryl tricaprylate, glyceryl triundecylate, glyceryl triisopalmitate, glyceryl triisostearate, octyldodecyl neopentanoate, isostearyl octanoate, octyl isononanoate, hexyldecyl neodecanoate, octyldodecyl neodecanoate, isocetyl isostearate, isostearyl isostearate, octyldecyl isostearate, polyglyceryl oleate, polyglycerol Glycerin isostearate, dipropyl carbonate, dialkyl carbonate (C12-18), triisocetyl citrate, triisoaralkyl citrate, triisooctyl citrate, lauryl lactate, myristyl lactate, cetyl lactate, octyldecyl lactate, triethyl citrate, acetyltriethyl citrate, acetyltributyl citrate, trioctyl citrate, diisostearyl malate, 2-ethylhexyl hydroxystearate, di(2-ethylhexyl) succinate diisobutyl adipate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoyl hydroxystearate, stearyl 12-stearoyl hydroxystearate, isostearyl 12-stearoyl hydroxystearate, etc.

Hydrocarbon-type oil phase ingredient: squalene, liquid paraffin, α-olefin oligomer, isoparaffin, ceresin, paraffin, liquid isoparaffin, polybutene, microcrystalline wax, Vaseline or the like.

Animal and Plant Oil, Hardened Oil thereof, and Wax of Natural Origin:

Animal oils and hardened oils thereof, such as beef tallow, hardened beef tallow, lard, hardened lard, horse oil, hardened horse oil, mink oil, orange roughy oil, fish oil, hardened fish oil, egg yolk oil or the like; plant oils and hardened oils thereof such as avocado oil, almond oil, olive oil, cacao oil, kiwifruit seed oil, apricot kernel oil, kukui nut oil, sesame oil, wheat germ oil, rice germ oil, rice bran oil, safflower oil, shea butter, soybean oil, evening primrose oil, perilla oil, tea seed oil, tsubaki oil (camellia japonica oil), corn oil, rapeseed oil, hardened rapeseed oil, palm kernel oil, hardened palm kernel oil, palm oil, hardened palm oil, peanut oil, hardened peanut oil, castor oil, hydrogenated castor oil, sunflower oil, grape seed oil, jojoba oil, hardened jojoba oil, macadamia nut oil, meadowfoam seed oil, cottonseed oil, hardened cottonseed oil, coconut oil, hardened coconut oil, or the like; and waxes such as beeswax, high acid number beeswax, lanolin, reduced lanolin, hardened lanolin, liquid lanolin, carnauba wax and montan wax, or the like.

Silicone-type oil phase ingredient includes: dimethylpolysiloxane, methylphenylpolysiloxane, methylcyclopolysiloxane, octamethylpolysiloxane, decamethylpolysiloxane, dodecamethylcyclosiloxane, methylhydrogenpolysiloxane, polyether-modified organopolysiloxane, dimethylsiloxane and methylcetyloxysiloxane Polymer, dimethylsiloxane/methylstearoxysiloxane copolymer, alkyl-modified organopolysiloxane, terminal-modified organopolysiloxane, amino-modified silicone oil, amino-modified organopolysiloxane, dimethiconol, silicone gel, acrylic silicone, trimethylsiloxysilicic acid, Silicone RTV rubber, etc.

Fluorine-type oil phase ingredient includes: perfluoropolyether, fluorine-modified organopolysiloxane, pitch fluoride, fluorocarbon, fluoroalcohol, fluoroalkyl/polyoxyalkylene co-modified organopolysiloxane, or the like.

(2) Specific Examples of Higher Alcohol

Lauryl alcohol, myristyl alcohol, cetyl alcohol, stearyl alcohol, isostearyl alcohol, oleyl alcohol, behenyl alcohol, 2-ethylhexanol, hexadecyl alcohol and octyl dodecanol or the like.

(3) Specific Examples of Fatty Acids

Caprylic acid, capric acid, undecylenic acid, lauric acid, myristic acid, palmitic acid, palmitoleic acid, stearic acid, isostearic acid, oleic acid, linoleic acid, linolenic acid, arachic acid, arachidonic acid, behenic acid, erucic acid, 2-ethylhexanoic acid or the like.

(4) Specific Examples of Ultraviolet Absorber

Para-aminobenzoic acid, amyl para-aminobenzoate, ethyldihydroxypropyl para-aminobenzoate, glyceryl para-aminobenzoate, ethyl para-aminobenzoate, octyl para-aminobenzoate, octyldimethyl para-aminobenzoate, ethylene glycol salicylate, octyl salicylate, triethanolamine salicylate, phenyl salicylate, butylphenyl salicylate, benzyl salicylate, homomenthyl salicylate, benzyl cinnamate, octyl para-methoxycinnamate, 2-ethylhexyl para-methoxycinnamate, glyceryl mono-2-ethyl hexanoate di-para-methoxycinnamate, isopropyl para-methoxycinnamate, diethanolamine para-methoxyhydrocinnamate, diisopropyl diisopropylcinnamic acid ester mixture, urocanic acid, ethyl urocanate, hydroxymethoxybenzophenone, hydroxymethoxybenzophenone sulfonic acid and a salt thereof, dihydroxymethoxybenzophenone, sodium dihydroxymethoxybenzophenone-disulfonate, dihydroxybenzophenone, dihydroxydimethoxybenzophenone, hydroxyoctoxybenzophenone, tetrahydroxybenzophenone, butylmethoxydibenzoylmethane, 2,4, 6-trianilino-p-(carbo-2-ethylhexyl1-oxy) 1, 3,5-triazine, 2-(2-hydroxy-5-methylphenyl) benzotriazole, methyl-0-aminobenzoate, 2-ethylhexyl-2-cyano-3,3-diphenylacrylate, phenylbenzimidazole sulfuric acid, 3-(4-methylbenzylidene) camphor, isopropyldibenzoylmethane, 4-(3, 4-dimethoxyphenylmethylene)-2, 5-doxy-1-imidazolidinepropionate, and polymer derivatives and silane derivatives thereof, or the like.

(5) Specific Examples of Powder and Pigment Pigments such as Food Red 104, Food Red 201, Food Yellow 4, Food Blue 1 and Food Black 401; lake pigments such as Food Yellow 4 AL lake and Food Yellow 203 BA lake; polymers such as nylon powder, silk powder, urethane powder, Teflon® powder, silicone powder, polymethyl methacrylate powder, cellulose powder, starch, silicone elastomer spherical powder and polyethylene powder; color pigments such as yellow iron oxide, red iron oxide, black iron oxide, chromium oxide, carbon black, ultramarine and iron blue; white pigments such as zinc oxide, titanium oxide and cerium oxide; extender pigments such as talc, mica, sericite, kaolin and plate barium sulfate; pearl pigments such as mica titanium; metal salts such as barium sulfate, calcium carbonate, magnesium carbonate, aluminum silicate and magnesium silicate; inorganic powders such as silica and alumina; metal soaps such as aluminum stearate, magnesium stearate, zinc palmitate, zinc myristate, magnesium myristate, zinc laurate and zinc undecylenate; bentonite; smectite; and boron nitride. From among the above ingredients, one only can be used, or two or more can be used together.

The shape (e.g., sphere, bar, needle, plate, amorphous, scale, spindle) and the particle size of these powders are not particularly limited. These powders may or may not be previously surface treated by a conventionally known surface treatment such as fluorine compound treatment, silicone treatment, silicone resin treatment, pendant treatment, saline coupling agent treatment, titanium coupling agent treatment, lubricant treatment, N-acylated lysine treatment, polyacrylic acid treatment, metal soap treatment, amino acid treatment, lecithin treatment, inorganic compound treatment, plasma treatment and mechanochemical treatment.

(6) Specific Examples of Surfactants

Anionic Surfactant:
Fatty-acid soap, a-acyl sulfonate, alkyl sulfonate, alkyl-allyl sulfonate, alkylnaphthalene sulfonate, alkyl sulfate, POE alkyl ether sulfate, alkylamide sulfate, alkyl phosphate, POE alkyl phosphate, alkylamide phosphate, alkyloylalkyl taurine salt, N-acylamino acid salt, POE alkyl ether carbonate, alkyl sulfosuccinate, sodium alkylsulfoacetate, acylated hydrolyzed collagen peptide salt, perfluoroalkylphosphoric acid ester or the like.

Cationic Surfactant:
Alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyltrimethylammonium bromide, benzalkonium chloride, behenic acid amidopropyldimethyl hydroxypropylammonium chloride, diethylaminoethylamide stearate, dimethylaminoethylamide stearate, dimethylaminopropylamide stearate, lanolin derivative quaternary ammonium salt or the like.

Amphoteric Surfactant:
Carboxybetaine type, amidobetaine type, sulfobetaine type, hydroxysulfobetaine type, amidosulfobetaine type, phosphobetaine type, aminocarboxylate type, imidazoline derivative type, amidoamine type or the like.

Nonionic Surfactant:
Propylene glycol fatty-acid ester, glycerin fatty-acid ester, polyglycerin fatty-acid ester, sorbitan fatty-acid ester, POE sorbitan fatty-acid ester, POE sorbitol fatty-acid ester, POE glycerin fatty-acid ester, POE alkyl ether, POE fatty-acid ester, POE hydrogenated castor oil, POE castor oil, POE-POP copolymer, POE-POP alkyl ether, polyether-modified silicone lauric acid alkanolamide, alkylamine oxide, hydrogenated soybean phospholipid or the like.

Natural-Type Surfactant:
Lecithin, saponin, sugar-type surfactant or the like.

(7) Specific Examples of Polyhydric Alcohol and Sugar

Ethylene glycol, diethylene glycol, polyethylene glycol, propylene glycol, dipropylene glycol, polypropylene glycol, glycerin, diglycerin, polyglycerin, 3-methyl-1, 3-butanediol, 1,3-butylene glycol, sorbitol, mannitol, raffinose, erythritol, glucose, sucrose, fruit sugar, xylitol, lactose, maltose, maltitol, trehalose, alkylated trehalose, mixed isomerized sugar, sulfated trehalose, pullulan or the like. Chemically modified products thereof can also be used.

(8) Specific Examples of Polymer Compound

Anionic polymer compounds such as acrylic acid ester/methacrylic acid ester copolymer (PLUS-SIZE, produced by Sogokagaku K. K.), vinyl acetate/crotonic acid. copolymer (Resin 28-1310, produced by NSC), vinyl acetate/crotonic acid/vinyl neodecanate copolymer (28-2930, produced by NSC), methyl vinyl ether maleic acid half ester (GANTREZ ES, produced by ISP), T-butyl acrylate/ethyl acrylate/methacrylic acid copolymer (RUBIMER, produced by BASF), vinylpyrrolidone/vinyl acetate/vinyl propionate copolymer (RUBISCOL VAP, produced by BASF), vinyl acetate/crotonic acid copolymer (RUBISET CA, produced by BASF), vinyl acetate/crotonic acid/vinylpyrrolidone copolymer (RUBISET CAP, produced by BASF), vinylpyrrolidone/acrylate copolymer (RUBIFLEX, produced by BASF), acrylate/acrylamide copolymer (ULTRAHOLD, produced by BASF), vinyl acetate/butyl maleate-isobornyl acrylate copolymer (ADVANTAGE, produced by ISP), carboxy vinyl polymer (CARBOPOL, produced by BF Goodrich) and acrylic acid-alkyl methacrylate copolymer (PAMUREN, produced by BF Goodrich); amphoteric polymer compounds such as acetic acid amphoteric compound of dialkylaminoethyl methacrylate polymer (YUKAFORMER, produced by Mitsubishi Chemical) and octylacrylamide acrylate/hydroxypropyl acrylate/butylaminoethyl methacrylate copolymer (AMPHOMER, produced by NSC); cationic polymer compounds such as quaternized compound of vinylpyrrolidone/dimethylaminoethyl methacrylate (GAFQUAT, produced by ISP) and methyl vinyl imidazolium chloride/vinylpyrrolidone copolymer (RUBICOTE, produced by BASF); and nonionic polymer compounds such as polyvinylpyrrolidone/vinyl acetate copolymer (RUBISCOL VA, produced by BASF) and vinylpyrrolidone/dimethylaminoethyl methacrylate copolymer (COPOLYMER VC7I3, produced by ISP).

In addition, polymer compounds of natural origin, such as cellulose and derivatives thereof, calcium alginate, pullulan, agar, gelatin, tamarind seed polysaccharides, xanthane gum, carrageenan, high-methoxyl pectin, low-methoxyl pectin, guar gum, gum arabic, crystal cellulose, arabino galactan, karaya gum, tragacanth gum, alginic acid, albumin, casein, cardrun, gellan gum, dextran or the like, can also be suitably used.

(9) Specific Examples of Biologically Active Ingredients

The biologically active ingredient may include substances that are capable of imparting some biological activity to skin when such a substance is applied to the skin. Specific examples thereof may include; whitening ingredient, anti-inflammatory agent, age resistor, ultraviolet protection, slimming agent, skin tightening agent, antioxidant, hair restorer, hair growing agent, moisturizer, blood circulation accelerator, antibacterial agent, bactericide, desiccant, cooling agent, warming agent, vitamin compound, amino acid, wound healing accelerator, torpent, analgetic, cell activator and enzyme ingredient.

Suitable examples of the ingredient to be blended therefor may include: angelica extract, avocado extract, hydrangea extract, althea extract, arnica extract, aloe extract, apricot extract, apricot core extract, ginkgo extract, fennel extract, turmeric extract, oolong tea extract, rose fruit extract, echinacea leaf extract, scutellaria root extract, phellodendron bark extract, goldthread extract, barley extract, hypericum extract, white nettle extract, watercress extract, orange extract, sea salt, seaweed extract, hydrolyzed elastin, hydrolyzed wheat powder, hydrolyzed silk, chamomile extract, carrot extract, artemisia capillaris extract, glycyrrhiza extract, Hibiscus sabdariffa extract, pyracantha fortuneana fruit extract, kiwi fruit extract, cinchona extract, cucumber extract, guanosine, gardenia extract, sasa albo-marginata extract, sophora root extract, walnut extract, grapefruit extract, clematis extract, chlorella extract, mulberry bark extract, gentian extract, black tea extract, yeast extract, burdock extract, fermented rice bran extract, rice germ oil, comfrey extract, collagen, cowberry extract, asiasarum root extract, bupleurum falcatum root extract, umbilical cord extract, salvia extract, saponaria extract, bamboo grass extract, crataegus extract, zanthoxylum fruit extract, shiitake mushroom extract, rehmannia root extract, lithospermum root extract, perilla extract, linden extract, filipendula extract, peony root extract, calamus rhizome extract, birch extract, horsetail extract, ivy extract, hawthorn extract, sambucus nigra extract, yarrow extract, peppermint extract, sage extract, mallow extract, cnidium rhizome extract, swertia herb extract, soy extract, jujube extract, wild thyme extract, green tea extract, clove extract, cogon extract, citrus unshiu peel extract, angelica root extract, calendula extract, peach seed extract, bitter orange extract, houttuynia extract, tomato extract, natto extract, ginseng extract, garlic extract, wild rose extract, hibiscus sabdariffa flower extract, ophiopogon tuber extract, parsley extract, honey, witch hazel extract, pellitory extract, isodonis extract, matricaria extract, loquat extract, coltsfoot extract, butterbur scape extract, Poria cocas extract, butcher bloom extract, grape extract, propolis, luffa extract, safflower extract, peppermint extract, linden extract, peony extract, hop extract, pine extract, horse chestnut extract, skunk cabbage extract, sapindaceae extract, balm mint extract, peach extract, cornflower extract, eucalyptus extract, saxifrage extract, coix seed extract, mugwort extract, lavender extract, apple extract, lettuce extract, lemon extract, Chinese milk vetch extract, rose extract, rosemary extract, Roman chamomile extract, royal jelly extract, strawberry extract, long pepper extract, lotus leaf extract, Pfaffia extract, starfruit extract or the like.

Other examples may include biopolymers such as deoxyribonucleic acid, mucopolysaccharide, sodium hyaluronate, sodium, elastin, chitin, chitosan and hydrolyzed eggshell membrane; moisture retentive ingredients such as amino acid, hydrolyzed peptide, sodium lactate, urea, sodium pyrrolidonecarboxylate, betaine, whey and trimethylglycine; oily ingredients such as sphingolipid, ceramide, phytosphingosine, cholesterol, cholesterol derivatives and phospholipid; anti-inflammatory agent such as E-aminocaproic acid, glycyrrhizic acid, glycyrrhetic acid, lysozyme chloride, guaiazlene and hydrocortisone; vitamins such as vitamin A, vitamin B2, vitamin B6, vitamin D, vitamin E, calcium pantothenate, biotin and nicotinic acid amide; active ingredients such as allantoin, diisopropylamine dichloroacetate and 4-aminomethylcyclohexanecarboxylic acid; antioxidants such as tocopherol, carotenoid, flavonoid, tannin, lignin and saponin; cell activators such as a-hydroxy acid and hydroxy acid; blood circulation accelerators such as y-orizanol and vitamin E derivatives; wound healing agents such as retinol and retinol derivatives; whitening agents such as albumin, kojic acid, placenta extract, sulfur, ellagic acid, linoleic acid, tranexamic acid and glutathione; and hair growing agents such as cepharanthine, glycyrrhiza extract, capsicum tincture, hinokitiol, iodized garlic extract, pyridoxine hydrochloride, DL-a-tocopherol, DL-a-tocopheryl acetate, nicotinic acid, nicotinic acid derivatives, calcium pantothenate, D-pantothenyl alcohol, acetyl pantothenylethyl ether, biotin, allantoin, isopropylmethylphenol, estradiol, ethynyl estradiol, capronium chloride, benzalkonium chloride, diphenhydramine hydrochloride, Takanal, camphor, salicylic acid, vanillylamide nonylate, vanillylamide nonanoate, pyroctone olamine, glyceryl pentadecanoate, L-menthol, mononitroguaiacol, resorcinol, y-aminobutyric acid, benzethonium chloride, mexiletine hydrochloride, auxin, female hormone, cantharis tincture, cyclosporine, zinc pyrithione, hydrocortisone, minoxidil, polyoxyethylene sorbitan monostearate, peppermint oil and SASANISHIKI extract, or the like.

(10) Examples of Antioxidants

Plant extracts having an antioxidant effect, such as Sodium bisulfate, sodium sulfite, erythorbic acid, sodium erythorbate, dilauryl thiodipropionate, tocopherol, tolylbiguanide, nordihydroguaiaretic acid, parahydroxyanisole, butylhydroxyanisole, dibutylhydroxytoluene, ascorbyl stearate, palmitic acid, Ascorbyl, octyl gallate, propyl gallate, carotenoid, flavonoid, tannin, lignan, saponin, apple extract and clove extract, etc.

(11) Examples of Solvents

Purified water, ethanol, lower alcohol, ethers, LPG, fluorocarbon, N-methylpyrrolidone, fluoroalcohol, volatile linear silicone, next-generation fluorocarbon, etc.

Examples

Hereinafter, examples of the present invention will be described.

[Preparation of Seaberry (*Hippophae rhhamnoides L.*) Extract]

Dried fruits of Seaberry were crushed and immersed in a 5-fold weight of N-hexane with respect to the weight of the crushed fruit and defatted by stirring for one hour at a temperature of 20 to 40° C. Then solid-liquid separation was done using a centrifuge to obtain a defatted raw material.

Further, the defatted raw material was dried and extracted with 70 vol % hydrous ethanol having a volume of 7 times that of the dried defatted raw material, then stirred at a temperature of 70° C. or higher for one hour. After that, solid-liquid separation was done using a centrifuge. The extraction liquid was concentrated and dried, thus obtaining the seaberry extract.

[Preparation of Saw Palmetto Extract]

Saw palmetto extract can be prepared by a well-known extraction method using saw palmetto fruit as a raw material. In the Example, the saw palmetto extract used was a purified saw palmetto extract manufactured by Indena S.p.A.

Test Example: Evaluation of 5α-Reductase Inhibition

<Test Method>

The evaluation was done by the method shown below.

20 mM potassium phosphate buffer (pH6.5) containing 1 mM dithiothreitol, 3.5 μM testosterone, DMSO solution containing the test substance, 100 μM nicotinamide adenine dinucleotide phosphate (NADPH), 20 μg protein of female rat liver microsomes were added into 48 plates in the final volume of 500 μL/well.

DMSO was used instead of the test substance for the comparison of activity.

After incubating the reaction solution excluding microsomes at 37° C. for 10 minutes, the microsome solution was added and incubated at 37° C. for 30 minutes. Then, 5M aqueous sodium hydroxide solution was added to stop the enzymatic reaction. 450 μL of the reaction solution was transferred to a microtube, and then ethyl acetate was added for a partition extraction. Since testosterone should be transferred to the ethyl acetate layer, the ethyl acetate layer was transferred to a new microtube and exsiccated with a nitrogen gas stream. Then, 30 μL of a 60% methanol solution containing the internal standard substance dexamethasone (20 μg/mL) was added to dissolve the testosterone as the substrate. The testosterone concentration was then calculated from the testosterone/dexamethasone peak area ratio in solution using HPLC and internal standard method.

Test Example 1: 5α-Reductase Inhibitory Effect of Seaberry Extract

By the above method, the 5α-reductase inhibitory effect of the seaberry extract alone was first evaluated. Also, in Test Example 1, the saw palmetto extract alone, which is already known to have a 5α-reductase inhibitory effect, was similarly evaluated for 5α-reductase inhibitory effect. The results are shown in Table 1 below.

TABLE 1

5α-reductase inhibitory effect of seaberry extract alone and of saw palmetto extract alone

| | Inhibition (%) Enzyme (S9 Fraction) | | | | | | | |
|---|---|---|---|---|---|---|---|---|
| | − | + | + | + | + | + | + | |
| | Sample conc. (μg/mL) | | | | | | | IC50 |
| | 0 | 0 | 10 | 30 | 100 | 300 | 1000 | (μg/mL) |
| Seaberry extract | 100.0 ± 8.7## | 0.0 ± 4.7 | 6.7 ± 2.4 | 23.9 ± 3.1* | 38.6 ± 3.0** | 57.7 ± 6.2** | 70.9 ± 6.0** | 192.7 |
| Saw palmetto extract | 100.0 ± 9.6## | 0.0 ± 4.8 | 15.7 ± 2.4 | 57.9 ± 9.1** | 88.3 ± 5.9** | 67.1 ± 8.6** | 79.0 ± 3.4** | 24.4 |

Each value represents the means ± S.E.M (N = 3).

Asterisks denote significant differences from the normal group,

*p < 0.05,

**p < 0.01.

Results and Effects of Working Examples in Test Example 1

As shown in Table 1, as a result of evaluating the 5αreductase inhibitory activity of the seaberry extract, it was clarified that the seaberry extract had 5α-reductase inhibition at concentration of 30 μg/mL or more concentration-dependently. This confirmed that the seaberry extract is useful as a 5α-reductase inhibitor.

Test Example 2: Synergistic Effect of 5α-Reductase Inhibition by Saw Palmetto Extract and Seaberry Extract The synergistic effect of saw palmetto extract and seaberry extract was examined. The concentration of sawtooth extract was fixed at 30 μg/mL, the concentration of seaberry extract was adjusted to 0, 5, 10, 20, 30, 60 μg/mL, and the evaluation test of 5α-reductase inhibition was done in the same manner as above. The results will be shown in Table 2 below.

TABLE 2

5α-reductase inhibitory effect of seaberry extract alone and of mixture of seaberry extract and saw palmetto extract (synergistic effect) Inhibition (%)

| | Enzyme | | | | | | | |
|---|---|---|---|---|---|---|---|---|
| | − | + | + | + | + | + | + | + |
| | Sample conc. (μg/mL) | | | | | | | |
| | 0 | 0 | 0 | 5 | 10 | 20 | 30 | 60 |
| Seaberry extract | 100.0 ± 5.8## | 0.0 ± 2.5 | | −2.1 ± 3.2 | 16.0 ± 5.6 | 15.7 ± 8.4 | 29.6 ± 3.3** | 25.9 ± 3.4** |
| Seaberry extract + Saw palmetto extract 30 μg/mL | 100.0 ± 4.2## | 0.0 ± 5.1 | 43.9 ± 2.9 | 41.2 ± 14.6 | 87.5 ± 1.8 | 93.3 ± 4.8 | 85.6 ± 3.0 | 89.5 ± 0.9 |
| Compounding ratio (Saw palmetto extract:Seaberry extract) | | | | 6:1 | 3:1 | 3:2 | 1:1 | 1:2 |

Each value represents the means ± S.E.M (N = 3)

Results and Effects of Examples in Test Example 2

As shown in Table 2, when the 5α-reductase inhibitory action was compared to the seaberry extract alone and to the mixture of saw palmetto extract and seaberry extract, a synergistic effect was observed at 10 to 60 μg/mL of seaberry extract over 30 μg/mL of saw palmetto extract. By this result, it was confirmed that the mixture of the saw palmetto extract and the seaberry extract synergistically enhances the 5α-reductase inhibitory effect, and further confirmed that the synergistical effect is significant in the range of the compounding ratio by weight of the saw palmetto extract and of the seaberry extract (saw palmetto extract: seaberry extract) is 3~1:1~2, and is more significant in the range of 3:1~2 and the most significant in the range of 3:2. From this, it was confirmed that the mixture of saw palmetto extract and the seaberry extract is useful as a 5α-reductase inhibitor, and in particular, it is most useful as a 5α-reductase inhibitor in the above range of compounding ratios.

Examples of compounding the 5α-reductase inhibitor according to the present invention will be shown below. However, the present invention is not limited to them.

Blending Example 1: Chewing Gums

| | |
|---|---|
| Sugar | 53.0 wt % |
| Gum base | 20.0 |
| Glucose | 10.0 |
| Starch syrup | 16.0 |
| Aroma chemical | 0.5 |
| 5α-reductase inhibitor | 0.5 |
| | 100.0 wt % |

Blending Example 2: Gummies

| | |
|---|---|
| Reduction sugar | 40.0 wt % |
| Granulated sugar | 20.0 |
| Glucose | 20.0 |
| Gelatin | 4.7 |
| Water | 9.68 |
| Yuzu (Japanese citrus) juice | 4.0 |
| Yuzu flavor | 0.6 |
| Pigment | 0.02 |
| 5α-reductase inhibitor | 1.0 |
| | 100.0 wt % |

Blending Example 3: Candies

| | |
|---|---|
| Sugar | 50.0 wt % |
| Starch syrup | 33.0 |
| Water | 14.4 |
| Organic acid | 2.0 |
| Aroma chemical | 0.2 |
| 5α-reductase inhibitor | 0.4 |
| | 100.0 wt % |

Blending Example 4: Yogurt (Hard Type/Soft Type)

| | |
|---|---|
| Milk | 41.5 wt % |
| Powdered skim milk | 5.8 |
| Sugar | 8.0 |
| Agar-agar | 0.15 |
| Gelatin | 0.1 |
| Lactic-acid bacterium | 0.005 |
| 5α-reductase inhibitor | 0.4 |
| Aroma chemical | a minute amount |
| Water | the rest |
| | 100.0 wt % |

Blending Example 5: Soft Drinks

| | |
|---|---|
| Fructose-glucose solution | 30.0 wt % |
| Emulsifying agent | 0.5 |
| 5α-reductase inhibitor | 0.05 |
| Aroma chemical | appropriate amount |
| Distilled water | the rest |
| | 100.0 wt % |

Blending Example 6: Tablet-Shaped Sweets

| | |
|---|---|
| Sugar | 76.4 wt % |
| Glucose | 19.0 |
| Sucrose-acid ester | 0.2 |
| 5α-reductase inhibitor | 0.5 |
| Distilled water | 3.9 |
| | 100.0 wt % |

Blending Example 7: Soft Capsules

| | |
|---|---|
| Brown rice germ oil | 47.0 wt % |
| Yuzu (Japanese citrus) seed oil | 40.0 |
| Emulsifier | 12.0 |
| 5α-reductase inhibitor | 1.0 |
| | 100.0 wt % |

Blending Example 8: Tablets

| | |
|---|---|
| Lactose | 54.0 wt % |
| Crystalline cellulose | 30.0 |
| Starch-splitting product | 10.0 |
| Glycerin fatty-acid ester | 5.0 |
| 5α-reductase inhibitor | 1.0 |
| | 100.0 wt % |

Blending Example 9: Cosmetic Creams

| | |
|---|---|
| Squalene | 20.0 wt % |
| Beeswax | 5.0 |
| Refined jojoba oil | 5.0 |
| Glycerin | 5.0 |
| Glycerin monostearate | 2.0 |
| Polyoxyethylene (20) sorbitan monostearate | 2.0 |
| 5α-reductase inhibitor | 2.0 |
| Preservatives | appropriate amount |
| Aroma chemical | appropriate amount |
| Distilled water, | the rest |
| | 100.0 wt % |

Blending Example 10: Cosmetic Lotions

| | |
|---|---|
| Ethanol | 5.0 wt % |
| Glycerin | 2.0 |
| 1,3-butylene glycol | 2.0 |
| Polyethylene oleyl ether | 0.5 |
| Sodium citrate | 0.1 |
| Citric acid | 0.1 |
| 5α-reductase inhibitor | 0.1 |
| Distilled water | the rest |
| | 100.0 wt % |

Blending Example 11: Body Gel

| | |
|---|---|
| Macadamia nut oil | 2.0 wt % |
| Octyl dodecyl myristate | 10.0 |
| Methyl phenyl polysiloxane | 5.0 |
| Behenyl alcohol | 3.0 |
| Stearic acid | 3.0 |
| Bacillus alcohol | 1.0 |
| Glyceryl monostearate | 1.0 |
| Polyoxyethylene sorbitol tetraoleate | 2.0 |
| Hydrogenated soybean phospholipid | 1.0 |
| Ceramide | 0.1 |
| Retinol palmitate | 0.1 |
| Preservatives | appropriate amount |
| Centella asiatica extract | 1.0 |
| 5α-rreductase inhibitor | 1.0 |
| 1,3-butylene glycol | 5.0 |
| Distiled water | the rest |
| | 100.0 wt % |

Blending Example 12: Emulsion

| | |
|---|---|
| Squalene | 4.0 wt % |
| Vaseline | 2.5 |
| Cetanol | 2.0 |
| Glycerin | 2.0 |
| Proprietary oil type glycerin monostearate | 1.0 |
| Stearic acid | 1.0 |
| L-Arginine | 1.0 |
| 5α-reductase inhibitor | 0.5 |
| Potassium hydroxide | 0.1 |
| Aroma chemical | minute amount |
| Distiled water | the rest |
| | 100.0 wt % |

Blending Example 13: Bathing Agent (Liquid)

| | |
|---|---|
| Propylene glycol | 50.0 wt % |
| Ethanol | 20.0 |
| Sodium sulfate | 5.0 |
| 5α-reductase inhibitor | 0.5 |
| Lanolin | 0.5 |
| Avocado oil | 0.5 |
| Pigment | 1.5 |
| Aroma chemical | 22.0 |
| | 100.0 wt % |

Blending Example 14: Hair Growth Agent (Pharmaceutical Grade)

| | |
|---|---|
| 5α-reductase inhibitor | 5.5 wt % |
| Tocopherol acetate | 0.1 |
| Pantothenyl alcohol | 0.2 |
| Dipotassium glycyrrhizinate | 0.1 |
| Polyoxyethylene (EO60) hardened castor oil | 0.3 |
| Aroma chemical | 0.1 |
| Propylene glycol | 2.0 |
| Ethanol | 60.0 |
| Distiled water | the rest |
| | 100.0 wt % |

Blending Example 15: Hair Tonic

| | |
|---|---|
| Ethanol | 60.0 wt % |
| Polyoxyethylene hydrogenated castor oil | 0.5 |
| Glycerin | 3.0 |
| Menthol | 0.2 |
| 5α-reductase inhibitor | 0.3 |
| Aroma chemical and pigments | Appropriate amount |
| Ion-exchanged water | the rest |
| | 100.0 wt % |

INDUSTRIAL APPLICABILITY

As described above, the present invention has a 5α-reductase inhibitory action, which can suppress benign prostatic hyperplasia, prevent and improve androgenetic hair loss, and prevent and improve acne.

The invention claimed is:

1. A method for inhibiting 5α-reductase activity in a human body, comprising administering a saw palmetto extract and a seaberry extract to the human body in order to inhibit 5α-reductase activity, wherein a compounding ratio by weight of the saw palmetto extract and seaberry extract is 3:1-2 when administered, the administering using the compounding ratio showing a synergistic effect.

2. The method of claim 1, wherein a food or drink composition containing the saw palmetto extract and the seaberry extract is used for the administering to the human body.

3. The method of claim 1, wherein a cosmetic composition containing the saw palmetto extract and the seaberry extract is used for the administering to the human body.

* * * * *